United States Patent [19]
Tabari et al.

[11] Patent Number: 5,402,065
[45] Date of Patent: Mar. 28, 1995

[54] FOIL ASSEMBLY FOR MAGNETIC INSPECTION MACHINES

[75] Inventors: Mehrdad Z. Tabari; Roger P. Ashworth, both of Forest Hall, United Kingdom

[73] Assignee: British Gas plc, London, England

[21] Appl. No.: 960,060

[22] Filed: Oct. 14, 1992

[30] Foreign Application Priority Data

Oct. 14, 1991 [GB] United Kingdom ............... 9121744

[51] Int. Cl.6 .................. G01N 27/83; G01R 33/12
[52] U.S. Cl. ................................ 324/220; 324/262
[58] Field of Search ........................... 324/219–220, 324/239–243, 260–262

[56] References Cited

U.S. PATENT DOCUMENTS

| | | | |
|---|---|---|---|
| 3,593,122 | 7/1971 | Barton et al. | 324/220 |
| 4,105,972 | 8/1978 | Smith | 324/242 X |
| 4,310,796 | 1/1982 | Braithwaite et al. | 324/220 |
| 4,447,777 | 5/1984 | Sharp et al. | 324/220 |
| 4,855,676 | 8/1989 | Cecco et al. | 324/220 |

FOREIGN PATENT DOCUMENTS

| | | |
|---|---|---|
| 0051344 | 5/1982 | European Pat. Off. |
| 2034122 | 5/1980 | United Kingdom |

*Primary Examiner*—Gerard R. Strecker
*Assistant Examiner*—Warren S. Edmonds
*Attorney, Agent, or Firm*—Larson and Taylor

[57] ABSTRACT

The vehicle has two groups 24, 26 of foils which transfer flux to and return flux from a wall 10 of a pipeline. The flux is from a coil 20 or from a permanent magnet or magnets. Each group is a single group of common foil members 59 interleaved with spacers 69; or alternatively each group contains sets of common foil elements such as six sector-shaped sets, for example. Each foil 59 and each spacer 69 is cut from steel for example stainless steel. Each foil 25 is an outwardly-directed resiliently-deflectable foil integral with the common foil member forming an array around the vehicle. The foils are separated by slots 63 preferably V-shaped. The sets are clamped together by retainers 73 and pins 71. In the pipe 10 the foils deflect as indicated by broken lines 32, 34. The length of each foil is at least 200 times its thickness. The foil separation divided by their thickness is at least unity. Sensors 28 detect leakage flux due to metal loss from the wall.

8 Claims, 8 Drawing Sheets

FOIL ASSEMBLY FOR MAGNETIC INSPECTION MACHINES

The invention relates to magnetic inspection machines.

Magnetic inspection machines in the form of vehicles are used for inspecting the condition of pipelines and in such vehicles magnetic flux from permanent magnets or electromagnets is passed into and returned from the surrounding wall of the pipeline through steel bristles arranged in brush-like groups which sweep along the inside surface of the pipeline wall as the vehicle passes through the pipeline.

Each brush-like group of bristles comprises one or more relatively thick steel plates each having a set of holes. In each hole a tuft of steel bristles is secured. We have found that foils can be used instead of bristles and that for a given volume more metal is present when foils are used compared with the use of bristles. Also, the foils are secured by clamping them between members which allows the foils to be replaced without the need to replace plates corresponding to those on which the bristles are mounted.

Early proposals regarding foils are given in our British Patents Nos. 2034122 and 2086051. They explain that bristles or foils are required to be kept in contact with the wall of the pipeline despite variations in its internal diameter along its length.

Also, at least part of the weight of the vehicle and the forces due to movements of the vehicle transverse to the length of the pipeline are counteracted by the reactions between the pipeline wall and those bristles or foils which are forced towards wall by the weight or other forces.

As explained in those patents the proportion of the weight or such other forces imposed on the bristles or foils depends on the design of the vehicle.

In 2034122 the variations in the internal diameter of the pipeline wall are accommodated by mounting the foil sets in pairs on respective magnetic return-path members, each member being connected to the body of the pig by springs.

In 2086051 the foils are described as being secured in fixed relationship to a common body member of the vehicle. However, the foils are described as being of the same kind as those disclosed in 2034122.

In 2034122 several foils are shown as integral parts of a common member 8. The foils are formed by slitting the common member at slits 11. The slits do not provide any clearance between neighbouring foils.

Foils can also be used in a magnetic inspection vehicle which is used to inspect the condition of tank floors and can also be used in a magnetic inspection machine which is used to inspect the condition of plates by relative motion between the foils and plates. In this specification the word "machine" means magnetic inspection machines in which plates are inspected and magnetic inspection vehicles for inspecting pipelines or for inspecting tank bases or floors.

A magnetic inspection machine according to the invention intended for progressively inspecting a workpiece, the machine moving past the workpiece or the workpiece moving past the machine, the machine comprising two groups of foils having tips which are intended to engage the workpiece and the groups being coupled magnetically at the ends of the foils remote from the tips to a source of magnetism, the foils being resiliently deflectable in a first direction transverse to the plane of the foil, each foil in each group being spaced from a neighbouring foil in said first direction by an intervening space and each foil in each group being separated from a neighbouring foil in a second direction transverse to said first direction by an intervening slot.

Embodiments of the invention will now be described by way of example with reference to the accompanying drawings, in which.

FIGS. 1 to 5 show a magnetic inspection machine in the form of a pipeline inspection vehicle for inspecting ductile cast iron gas distribution pipelines, in this case 12" pipelines (i.e. pipelines having nominally a 12", 300 millimeter inside diameter). The invention is applicable to vehicles for inspecting different sized pipelines, e.g. 6" and 8" gas distribution pipelines, and also steel gas transmission lines having inside diameters of, say, 6" and above. The invention is also applicable to vehicles for inspecting non-gas pipelines, such as steel water or oil or other pipelines, for example.

In this example, the pipeline is inspected while it is "dead" i.e. without any gas being present in it and the vehicle is intended to be pulled through the pipeline by a cable attached to a winch. In transmission lines, the vehicle would normally be equipped with cups engaging the pipe wall and the vehicle would be propelled by a difference in pressure (developed across the cups) in the product being conveyed by the pipeline.

Other drive options which are possible include the use of a tethered vehicle driven by drive cups engaging the pipe wall (e.g. the vehicle could be tethered by the umbilical cable). The pressure difference across the cups may be due to air or other fluid blown along the pipe, in the inspection of "dead" pipelines, or where the pressure would be high enough the pressure difference across the cups could be due to gas moving in the pipeline as in medium pressure (and higher) distribution lines; also included is the use of a tractor vehicle to pull the inspection vehicle or to have inspection facilities included in the tractor vehicle. A tractor vehicle is usable in gas distribution lines, gas transmission lines, and water or oil or other lines.

In further variations, tractor vehicles can react against the pipe wall, or react against a stationary "prelaid" cable if the pipewall cannot tolerate reaction forces.

Figure 1:
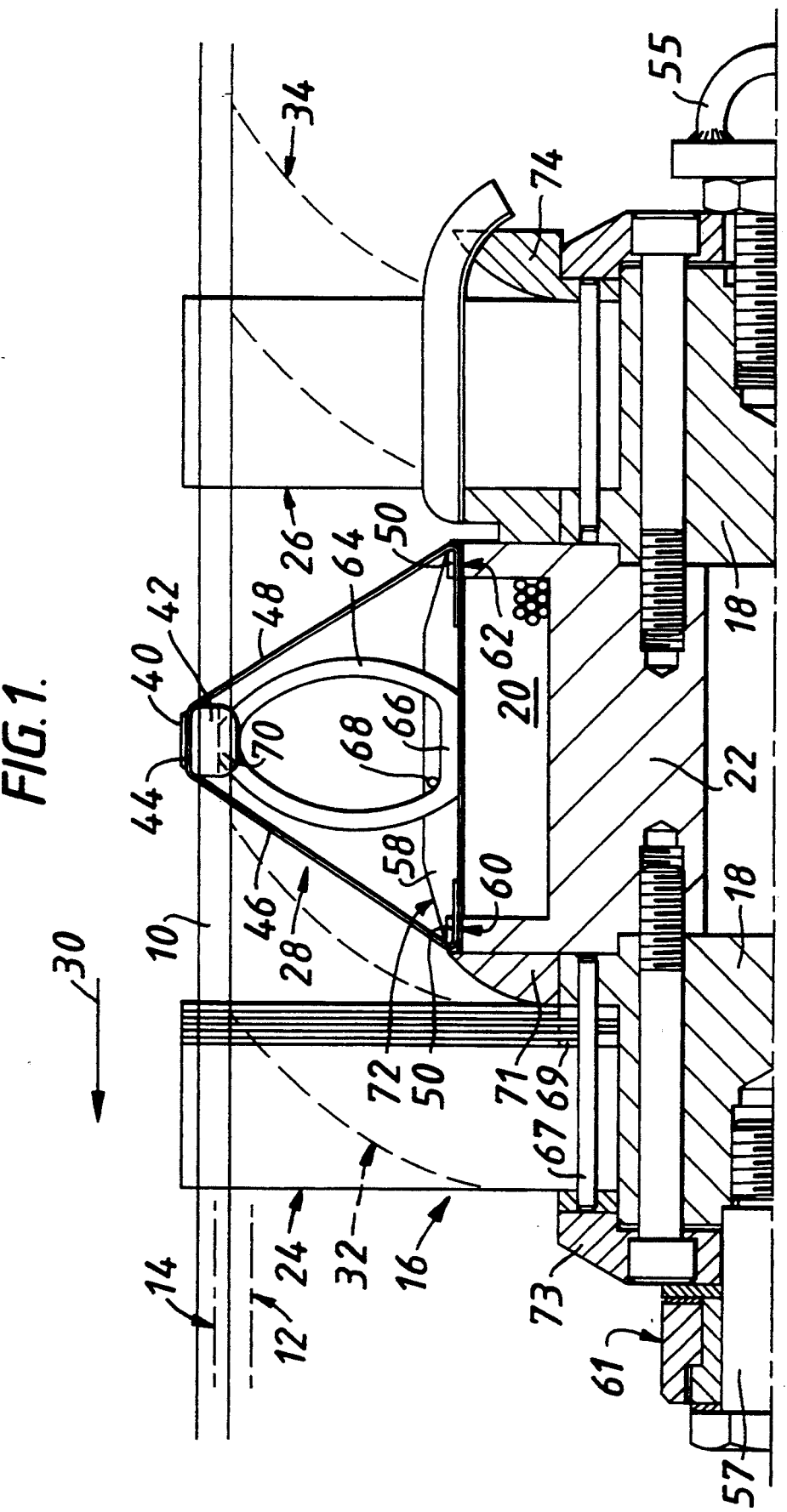
FIG. 1 is a vertical, longitudinal section through a first embodiment.

In FIG. 1, the minimum bore of the pipeline 10 is shown at 12 and the maximum bore of the pipeline 10 is shown at 14. The pipeline 10 is made of ductile cast iron and the bore varies between the maximum and minimum values shown.

The vehicle 16 consists of the following main components: a body 18; an electro-magnetic coil 20 wound on a former 22; groups of foils 24, 26; and thirty-six sensor assemblies 28 (only one of which is shown) equiangularly arranged around the body 18 of the vehicle 16.

Figure 2:
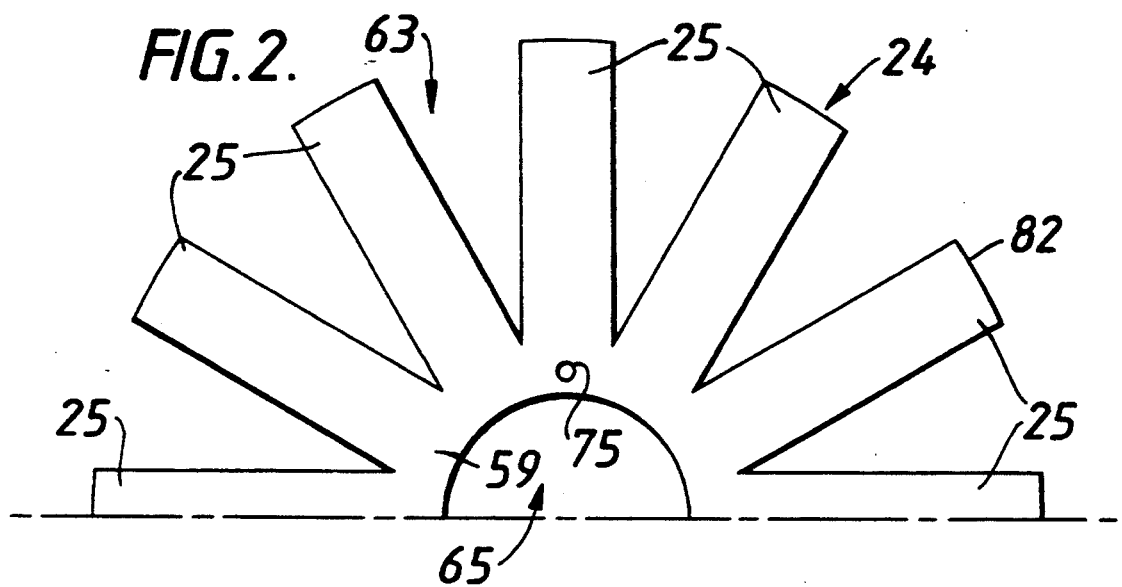
FIG. 2 is an elevation of foils used in the first embodiment.

Each group of foils 24, 26 is made up of a number of common foil members 59 each having the shape shown in FIG. 2. This shape preferably comprises twelve foils 25.

The use of foils gives a major advantage in that it allows a smaller occupied volume given the required metal area for adequate flux transmission into the pipe wall. In this specification each of the groups 24, 26 is referred to by the expression "flux conductor". The function of the groups of foils 24, 26 is explained below.

The vehicle in this case runs on the groups of foils without any other suspension component engaging the wall of the pipe. Alternative forms of vehicle may use wheels on the vehicle running along the pipewall in order to support all, or some of the weight of the vehicle. The wheels may be displaceable relative to the body against springs. Instead of, or in addition to, wheels the weight of the vehicle may be partly or wholly supported on the drive cups referred to above.

Each assembly 28 comprises an austenitic stainless steel sledge 40 which is secured to a sensor housing 42 with a length of belting 44 sandwiched between the two. The end portions of the belting 44 form a leading member 46 and a trailing member 48 which link the leading and trailing ends, respectively, of the sledge 40 to the vehicle. The belting 44 is made of polyurethane coated polyester fibres and is substantially inextensible.

The ends of the members 46, 48 are each held by a screw 50 which has a rounded head and retains a washer having a rounded edge portion against the belting 46 or 48. The screw 50 retains the member 46 or 48 against a stainless steel pressing 58 forming a base plate, itself retained in position on the outer edges 60, 62 of the former 22.

The assembly 28 is positioned against a spring 64, which is also positioned against the vehicle, or rather against the respective pressing or base plate 58. The spring 64 is approximately of 0 form and is made of polyurethane elastomeric material. The spring 64 has a flattened shape at 66 where it engages the base plate 58. The spring 64 is retained in position against the base plate 58 by a pin 68 which engages holes in the sides of the plate 58, which is of U-section. The spring 64 is retained at its opposite end by ears 70 formed on the sensor housing 42, the ears 70 extending one on each side of the spring 64 to retain it against sideways displacement normal to the plane of the spring 64.

The inspection vehicle 16 is shown in the condition which applies to the vehicle before it is inserted in the pipeline. Assuming the vehicle is intended to move in the direction of the arrow 30 shown in FIG. 1, when the vehicle 16 is inserted in the pipeline the foil groups 24, 26 would be deflected to the right so as to curve as indicated by the ghost outlines at 32 and 34.

The assemblies 28 would also be deformed and while the vehicle 16 is stationary in the pipeline, the members 46, 48 are slack and only the spring 64 is effective to exert a force on the sledge 40 which is substantially normal to the wall of the pipeline.

When the vehicle 16 moves (say in the direction of the arrow 30 shown in FIG. 1) the leading member 46 becomes taut and the motion of the vehicle is transmitted to sledge 40 by the member 16. The trailing member 48 becomes slack and does not play any part in the control of the assembly 28 so long as the sledge 40 runs along the inside of the pipewall.

When the sledge 40 travels across a void in the pipework (for example where a branch pipe joins the pipeline) the sledge 40 moves radially outwardly and both leading and trailing members 46, 48 act to exert inwardly directed forces on the sledge 40 to counteract the outward force of the spring 64.

The vehicle 16 is designed to travel backwards, should it prove impossible to move it forward. In that case, the roles of the members 46, 48 are reversed. The foil groups 24, 26 would be deformed in the opposite sense, curving towards the left instead of towards the right.

Figure 6:
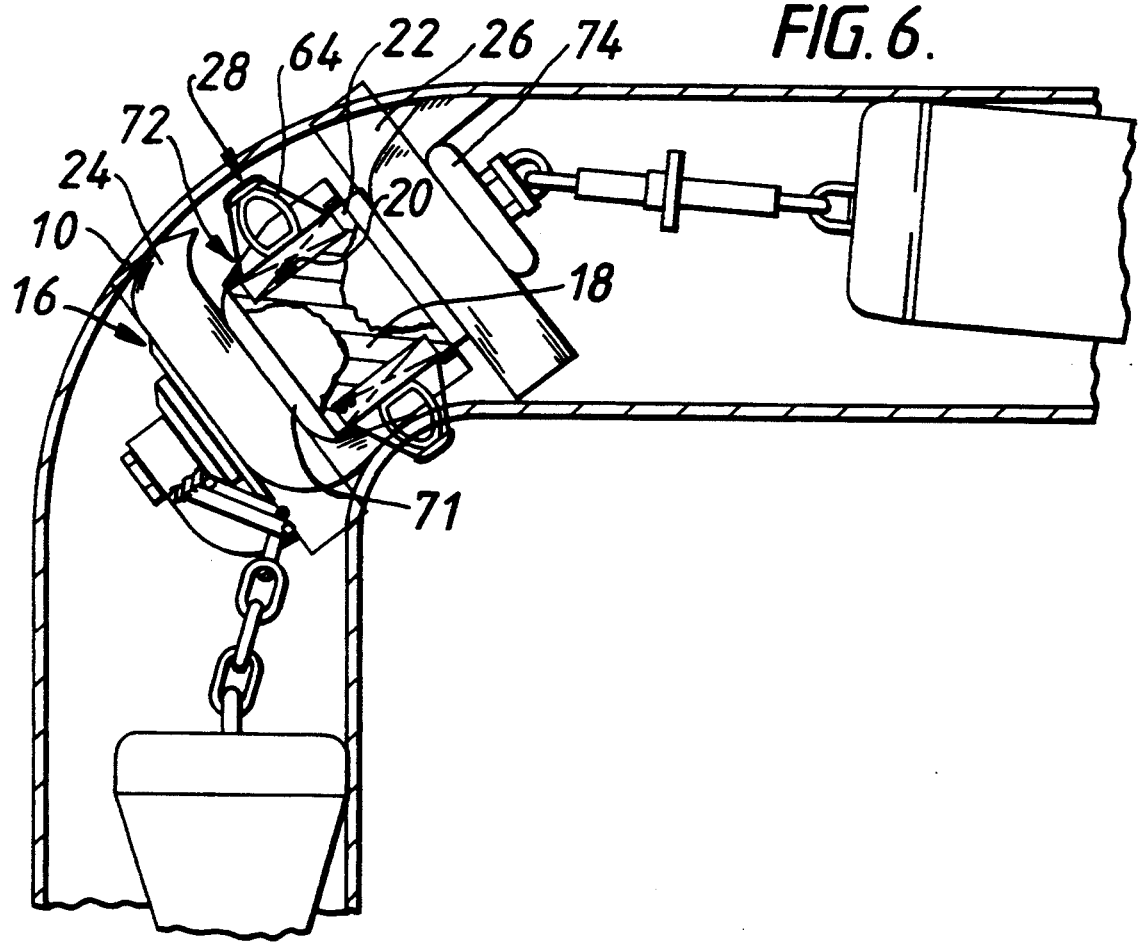
FIG. 6 shows a second embodiment.

Each assembly 28 must accommodate variations in the bore of the pipeline 10 and side-to-side motion of the vehicle within the pipeline. Furthermore, the vehicle is required to negotiate bends in the pipeline. Such bends may be as tight as one diameter, that is the radius of curvature of the bend (measured to the pipe centre) is equal to the internal diameter of the bend. Such a bend is especially severe in the case of 6" pipe. This is shown in FIG. 6 in which a 6" vehicle is shown negotiating a one diameter bend in a distribution pipeline. The assembly 28 at the inside of the bend is shown in the condition it has when the vehicle is outside the pipeline, however. In negotiating such a bend the sensor assembly 28 at the inside of the bend is required to collapse completely. This is possible owing to the nature of the leading and trailing members 46, 48. Under such conditions, the foil group 24 at the inside of the bend would be required to be deflected right over until the rearmost foil 25 lay against the stop 71 (shown in FIGS. 1 and 6) carried by the vehicle body 18, and against the upper edge 72, of the wings of the pressing 58. The foil group 26 would be heavily deformed, adjacent to the outer wall of the pipeline, and the rearmost foil 25 would conform to the stop 74 (shown in FIGS. 1 and 6) carried by the vehicle body 18.

Under certain conditions, the spring 64 might engage the leading member 46 and the trailing member 48.

For example, the size of the pipe might demand a spring of such characteristics that the spring occupies nearly the whole of the space between the leading member 46 and the trailing member 48. Under running conditions in the pipeline 10 the spring 64 might cause the leading member 46 to bow outwards.

However, even under such conditions the spring still exerts a force on the sledge 40 which is substantially normal to the pipewall. Also, the motion of the vehicle is still transmitted to the sledge 40 by the leading member 46 notwithstanding its bowed shape.

As shown, the vehicle 16 is intended normally to travel in the direction of the arrow 30 shown in FIG. 1, being pulled by a haulage cable (not shown) attached to a swivel assembly 61 mounted on a pin 57 secured to the leading end of the body 18. Another haulage cable (not shown) for retrieving the vehicle 16 in reverse is attached to the eye 55 secured to the trailing end of the body 18.

The inspection is carried out using the flux leakage method. A powerful magnetic field is generated by the electromagnetic coil 20 and transferred into, and out of, the wall of the pipeline 10 by the foil groups 24, 26. Electric current to energise the electromagnetic coil 20 is supplied from the surface via an umbilical supply cable (not shown) connected to the coil. Defects, such as loss of metal due to corrosion in the wall of the pipe, cause magnetic flux to leak out of the wall of the pipe and this is detected by the sensor within the housing 42. Each sensor transmits a continuous signal as the pie moves through the pipeline and this signal, with the signals from the other sensors, is sent down a second umbilical cable (not shown) which extends from the vehicle to a personal computer with a hard disc recording facility at the surface of the ground. The position of the vehicle along the pipeline is known from a monitor measuring the length of haulage cable paid out by the winch.

The vehicle does not inspect the condition of the pipewall as the vehicle negotiates 1-D bends, for example as shown in FIG. 6. However, for larger diameter bends where the sensors are able to run along the pipewall throughout the bend a full inspection is carried out. This will apply to most transmission pipeline inspections. It is only in distribution pipelines where 1-D and similar very tight bends are encountered that no inspection will be carried out in the region of the bends.

In some cases (for example where an umbilical supply cable cannot be used) the electromagnetic coil 20 is replaced by a permanent magnet or magnets.

The magnetic flux created by the electromagnet 20 circulates in a path, which includes the wall of the pipeline 10, the flux conductor or foil group 26, the return path provided by the body 18 and the other foil group 24 forming the other flux conductor.

In other modifications (not shown) the path may include flux return paths which are formed by members carried by the body, instead of the body itself providing the return path. For example, where permanent magnets are used instead of an electromagnet, the arrangement may be as shown in British patent specification No. GB-B-1535252. In that specification the magnets are flat plates having the magnetic poles at their broad faces and those faces are arranged parallel to the pipe inside surface. The magnets are arranged one at each end of flux return path members arranged around the body. The members are mounted on springs so as to move radially inward and outward to allow changes in diameter of the pipeline to be accommodated. The flux conductors are mounted upon the magnets. The assemblies 28 would in that arrangement be mounted not on the body itself but on a ring which is "floating". That is, the ring surrounds the flux return path members and is connected to them by radial posts which pass through holes in the ring. The ring can thus move radially with respect to the flux return path members as the vehicle negotiates bends.

Figure 3:
FIG. 3 is an edge-view of the foils shown in FIG. 2.
Figure 4:
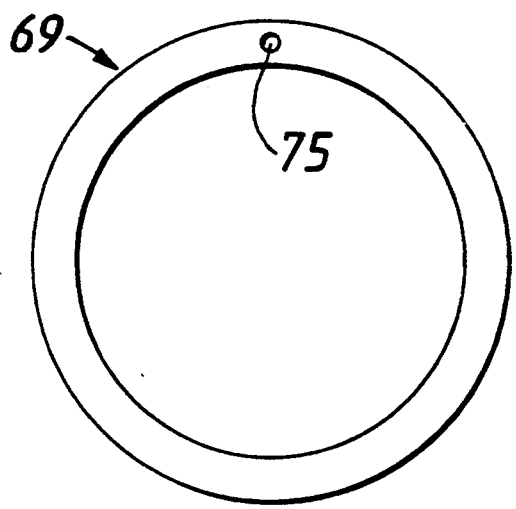
FIG. 4 is an elevation of a spacer used in the first embodiment.
Figure 5:
FIG. 5 is an edge-view of the spacer shown in FIG. 4.

Each group of foils 24, 26 consists of 90 foils each as shown in FIGS. 2 and 3. Each common foil member 59 is an annulus cut from sheet stainless ferritic or martensitic steel 0.3 mm thick, in this example. The overall diameter of each common foil member 59 is 345 mm in the undeflected condition of the common foil member 59. The groups of foils 24, 26 are shown undeflected, in full lines, in FIG. 1 and are also shown deflected as indicated by broken lines, 32.

Each common foil member 59 has twelve resiliently deflectable foils 25 separated by V-shaped intervening slots 63, the angle between adjacent fingers being 30 degrees. The central aperture 65 in each common foil member 59 has a nominal diameter of 90 mm. Each group of foils 24, 26 is located by the body 18 which extends through the central apertures 6 of the common foil member 59. In each group of foils 24, 26 adjacent common foil members 59 are separated by a single annular spacer 69 shown in FIGS. 1, 5 and 6. In this example, each spacer 69 is cut from the same sheet material as is used for the common foil members 59 and the external diameter of each spacer 69 is 125 mm. The internal aperture has a nominal diameter of 90 mm.

In each group of foils 24, 26 there is a pin 67 extending through holes 75 in the group. A retainer 73 retains the pin 67 and the group in position on the body 18.

Each spacer 69 is 0.3 mm thick. Thus, in this example, the quotient formed by dividing the separation of adjacent common foil members 59 in each group 24, 26 by the thickness of each common foil member 59 is unity. That quotient may be termed the "packing density".

The invention can be performed using foils and spacers of thickness different from the values quoted above by way of example. However, it is preferred that the packing density be equal to or greater than unity and it is particularly preferred that the packing density shall be in the range of from unity to two.

On an 8 inch vehicle the common foil members 59 (i.e. the foils 25) are preferably made from material which is 0.15 mm thick and the spacers 69 are preferably of the same thickness. On a 6 inch vehicle the common foil members 59 (i.e. the foils 25) are preferably made from material which is 0.075 mm thick and the spacers 69 are preferably of the same thickness. For an 8 inch vehicle there are preferably twelve foils on each common foil member 59, arranged equidistantly around the vehicle. The 8 inch vehicle preferably has twenty-four sensors. For a 6 inch vehicle there are preferably nine foils 25 on each common foil member 59, arranged equidistantly around the vehicle. The 6 inch vehicle preferably has eighteen sensors.

The outer edge of each spacer 69 just overlaps the innermost apices of the V-shaped slots 63 in the two adjacent common foil member 59 in the groups 24, 26 so that the free length of each foil 25 is 110 mm. The quotient formed by dividing the length of a foil 25 by its thickness in this example is 366. That quotient may be termed as the "slenderness ratio" of the foil. The invention can be performed using foils having dimensions different from those quoted above by way of example but it is preferred that the slenderness ratio be generally greater than 300. This is to avoid yielding of the material of the foil at large deflections.

The common foil members 59 in each group 24, 26 are arranged with their foils 25 aligned in trains 82. Each group 24, 26 accordingly comprises trains 82 of foils 25 separated by the aligned slots 63. Whilst it is preferred to have all the foils or at least most of them aligned in trains it is not essential and in other embodiments of the invention different arrangements can be used.

Whatever the arrangement, each group of foils comprise foils which form an array extending around the vehicle.

The first embodiment described above is intended for use in inspecting cast-iron natural gas distribution pipelines. The vehicle is pulled through the length of pipeline being inspected using a tow number 80 (FIG. 1) attached to a winch (not shown). The pipeline length is "dead" (i.e. no gas is flowing) during the inspection. The coil 20 is energised and produces magnetic flux which is conducted into the wall 10 of the pipeline and conducted back to the coil by the foil groups 24, 26. The groups are deflected as indicated in ghost outlines 32, 34 in FIG. 1 and slide along the inner surface of the wall 10. Loss of metal from the wall 10 owing to corrosion causes magnetic flux to leak from the wall 10 and the sensors 28 produced signals accordingly as they respond to the leakage flux. The signals pass to recording equipment (not shown) via an umbilical cable (not shown). Power is fed to the coil 20 via a power cable (not shown).

Figure 7:
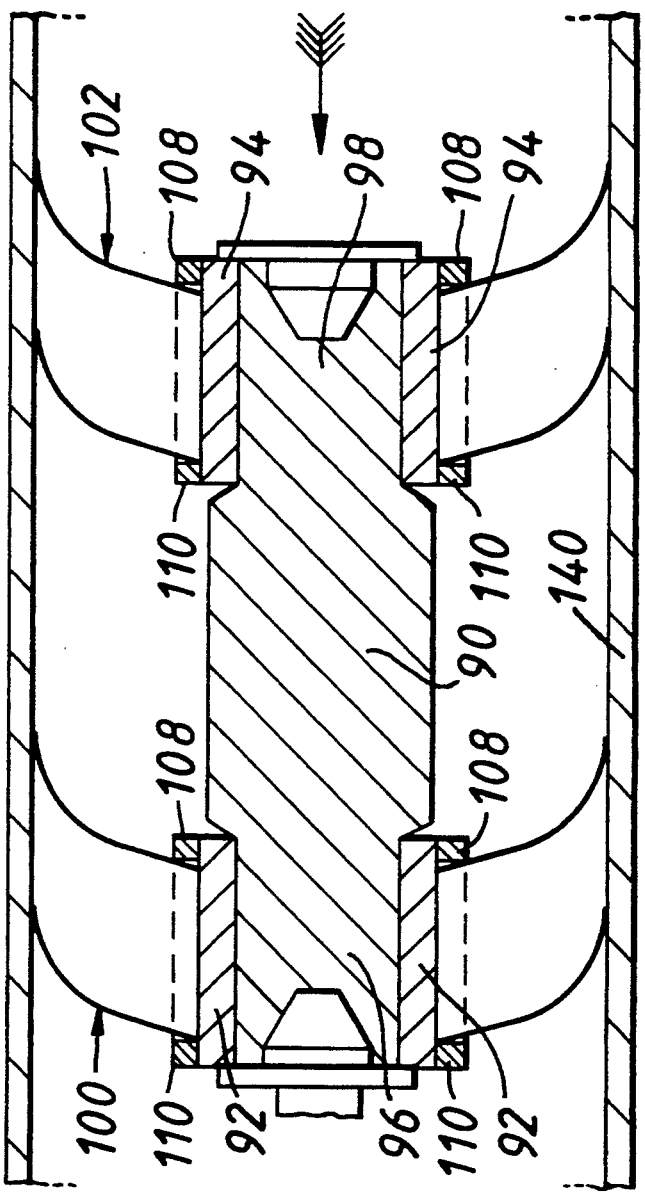
FIG. 7 is a vertical, longitudinal section through a third embodiment.
Figure 8:
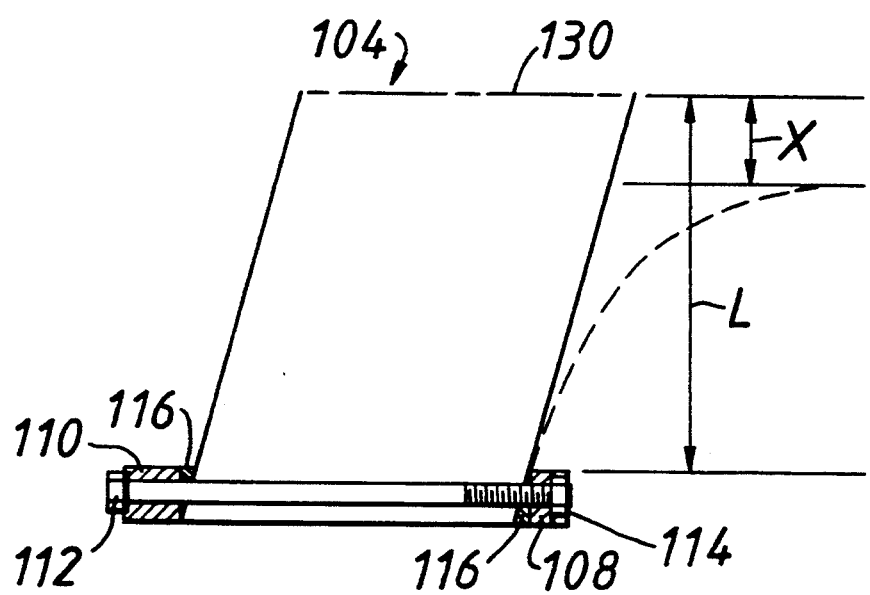
FIG. 8 is a scrap vertical section through a set of foils, shown undeflected, used in the third embodiment.
Figure 9:
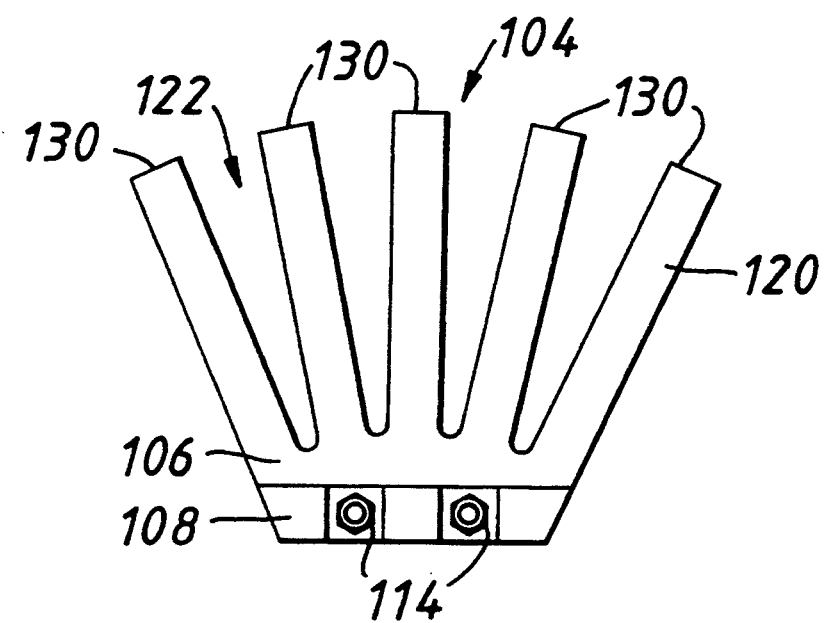
FIG. 9 is a scrap elevation of the set of foils shown in FIG. 8.

A second embodiment of vehicle is shown in FIGS. 7 to 9. The vehicle is intended to be used for "on-line" inspection of a transmission pipeline i.e. a pipeline which is conducting natural gas or oil or some other product under pressure. Typically, for example, such a pipeline has an internal diameter varying in the range 416 to 446 mm and the vehicle would be used in train with one or more other vehicles making up a "pig". The pig is moved through the pipeline by the pressure difference developed across the pig by the fluid flowing in the pipeline. For example, one of the vehicles in the pig train can be fitted with rubber seal cups which slide along the inside surface of the pipeline and the pressure difference across at least one cup propels the pig.

The vehicle comprises: a solid body 90 of mild steel; two sets of permanent magnets 92, 94 each magnet being secured to a flat face of a hexagonal-shaped end portion 96, 98 of the body 90; and two groups of foils 100, 102 secured to the magnets 92, 94, respectively.

Magnetic field sensors, which would be mounted on the vehicle have been omitted from FIGS. 7 to 9.

Each group of foils 100, 102 is made up of six sets 104 of common foil members (FIGS. 8 and 9). Each set 104 comprises in this example 175 common foil members 106 clamped together with intervening spacers (not shown) which each have the same outline shape as one of the clamp blocks 108. The common foil members 106 are clamped between the block 108 and a second block 110 by bolts 112 and nuts 114, together with tapered end spacers 116.

Each common foil member 106 is sector-shaped and comprises five integral resiliently deflectable foils 120 separated by V-shaped slots 122. Typically, in this example, the width of the narrower, lower end of each common foil member 106 is 140 mm and the maximum free length of each foil 120 is 110 mm. The common foil members 106 and spacers are each 0.3 mm thick. The packing factor is thus unity and the slenderness ratio is 367. The angle between the two outermost foils 120 is 48 degrees and the angle between adjacent foils is 12 degrees. When the six sets 104 are made up into a group 100 or 120 of foils the angle between the adjacent foils 120 in adjacent sets is also 12 degrees. The distance between the leading the trailing ends of the set of foils shown in FIG. 8 measured between the tapered spacers 116 is 105 mm.

The clamping blocks 108, 110 are secured to the magnets 92 or 94.

The foils are shown undeflected in FIGS. 8 and 9. Each group of foils 100, 102 comprises common foil members 106 which form an array extending around the vehicle. In this example the foils in each group are arranged with the foils 120 aligned in trains 130 separated by the aligned slots 122. However, as already explained, that is not essential.

The common foil members 106 in this example are inclined in each group 100, 102 so that their outer ends are positioned, even in the undeflected condition, rearwardly with respect to their inner ends in relation to the direction of forward motion of the vehicle indicated by the arrow in FIGS. 7 and 8. Such sweeping back of the foils 120 is preferred but it is not essential. It is a design option which can be used to reduce the drag imposed by the foils on the vehicle.

FIG. 7 shows the foils in the groups 100, 102 deflected by engagement with the wall 140 of the pipeline. Generally, in any embodiment, it is preferred that in the working range of deflections the radial strain to which the foils are subjected is up to 30%, depending on the packing density. The radial strain is defined as the quotient $X/L100\%$, where L is the free undeflected "height" of the foil as indicated in FIG. 8 and X is the difference between L and the deflected height of the foil.

Figure 10:
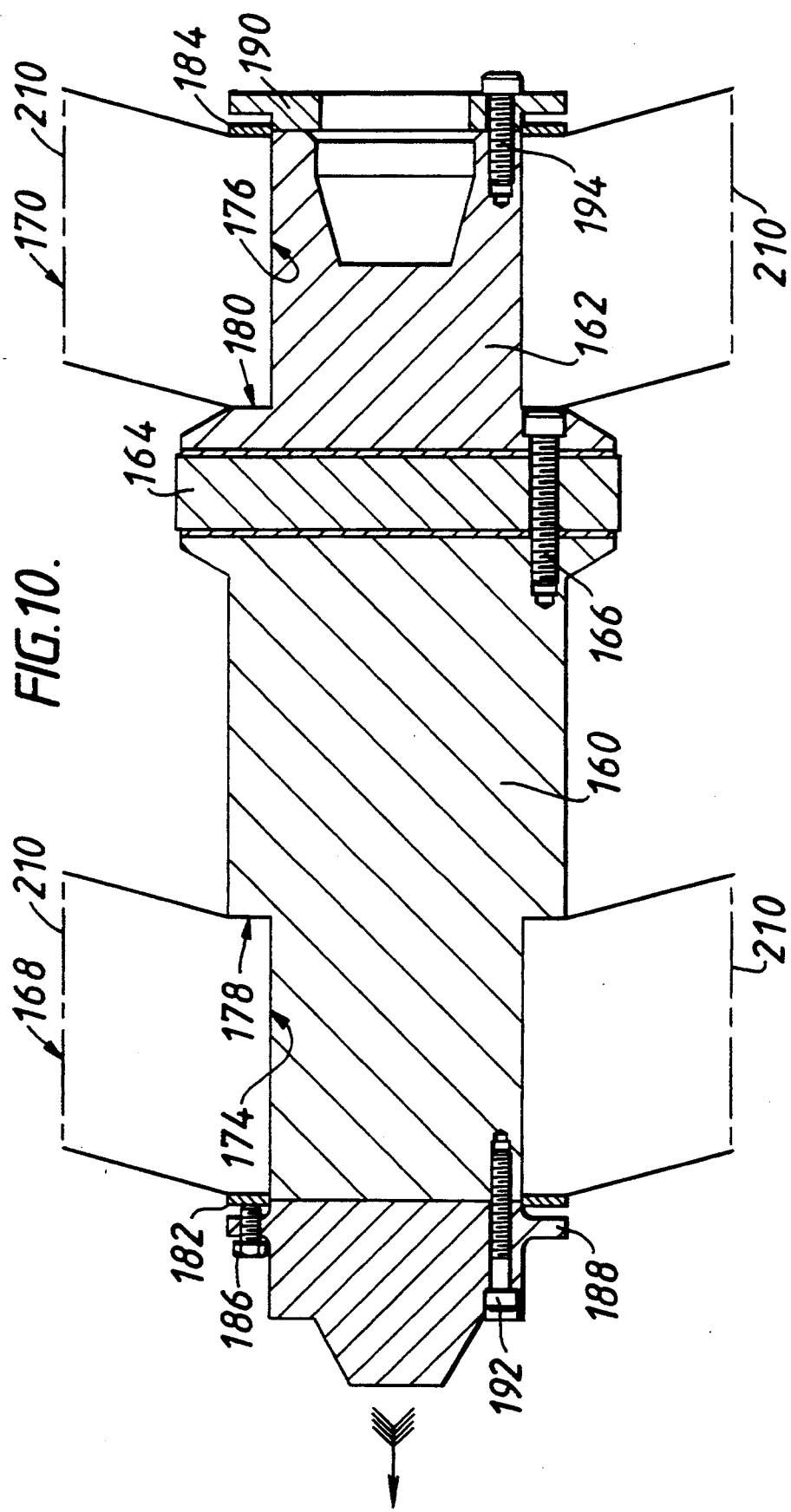
FIG. 10 is a vertical longitudinal section through a fourth embodiment.
Figure 11:
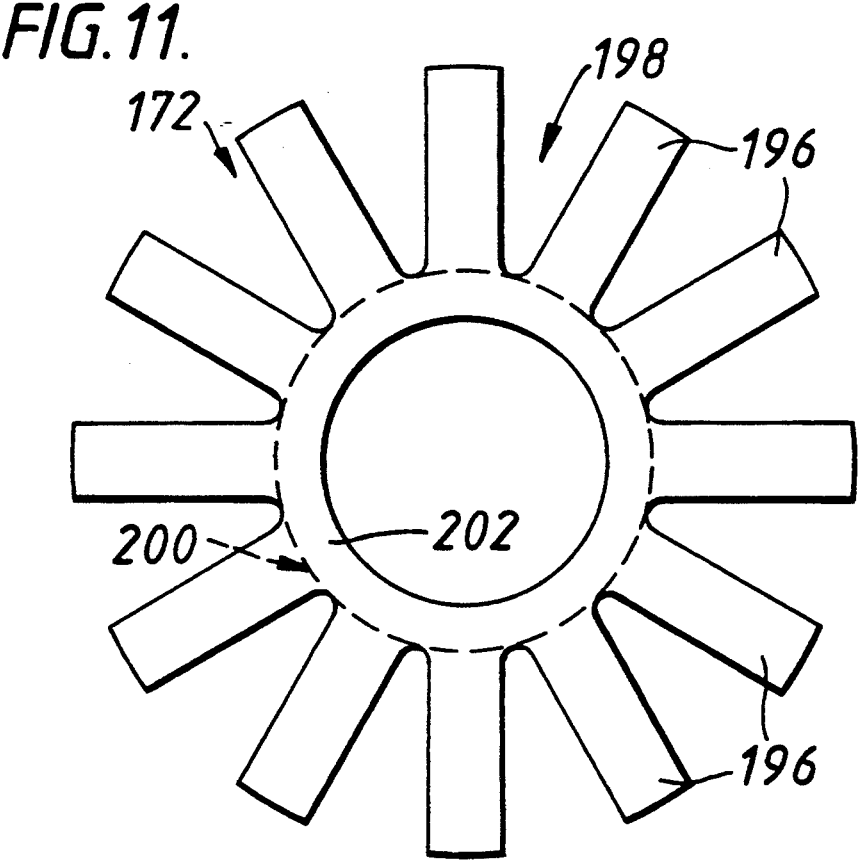
FIGS. 11 and 12 are, respectively, an elevation and an edge view of a foil used in the embodiment shown in FIG. 10.
Figure 12:
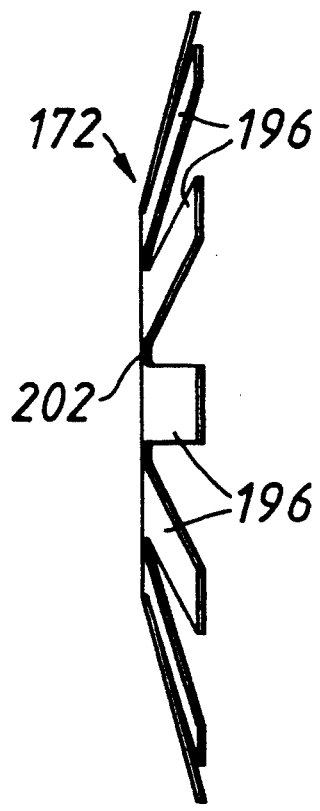

In the third embodiment shown in FIGS. 10 to 12 the vehicle is typically for example intended for use in inspecting a transmission pipeline of nominally 204 mm (8 inches) internal diameter. The vehicle has a body made up of two solid cylindrical mild steel parts 160, 162 with an annular permanent magnet 164 between them, the assembly being held together by bolts 166. The vehicle has two groups of foils 168, 170 each group comprising a single common foil member 172 (FIGS. 11 and 12). Each common foil member 172 is annular and is located on a reduced diameter portion 174 or 176 on the body parts 160, 162. The magnetic field sensors which would be mounted on the vehicle have been omitted from FIGS. 10 to 12.

The groups of common foil members are clamped, with intervening annular spacers (not shown) which also encircle the reduced diameter portions, between shoulders 178, 180 on the parts 160, 162, respectively and rings, 182, 184. Each ring 182, 184 encircles the reduced diameter portion 174 or 176 and is forced against the group of common foil members by three screws such as the one shown at 186, the screws 186 being mounted in a further ring 188 or 190 secured to the relevant body part 160 or 162 by bolts 192 or 194.

Typically, in this example, each common foil member has a central aperture of 85 mm diameter and comprises twelve integral resiliently deflectable foils 196 separated by V-shaped slots 198. Each common foil member typically is cut from ferritic or martensitic stainless steel sheet 0.125 mm thick and the spacers (not shown) are cut from the same material. The packing density is thus unity. Any suitable material can be used for the common foil members, including mild steel.

The apices of the slots 198 coincide with the maximum diameter of each shoulder 178, 180 and of each ring 182, 184 such diameter being indicated by a broken line 200 in FIG. 11. Such diameter in this example is 115 mm.

The overall diameter of each common foil member 172 is typically in this example 235 mm and the foils 196 are each indicated at an angle of 15 degrees to the plane of the inner annular part 202 of the common foil member 172. The groups of foils 168, 170 are arranged so that the outer ends of the common foil member 172, even in their undeflected condition as shown in FIGS. 10 to 12, are positioned rearwardly with respect to their inner ends in relation to the direction of forward motion of the vehicle indicated by the arrow in FIG. 10.

When the vehicle is in its pipeline the groups of foils 168, 170 will be swept rearwardly in a manner analogous to that shown in FIG. 7. The length of each foil 196 in this example is 60 mm. The slenderness ratio is 480 mm. The foils are arranged in each group 168, 170 with the foils 196 aligned in trains 210 (FIG. 10) separated by the aligned slots 198. However, that is not essential.

The vehicle shown in FIGS. 9, 10 and 11 is intended for use in train with at least one other vehicle (not shown) to form a pig. The pig is propelled through the pipeline by fluid pressure difference developed as explained in relation to the second embodiment.

In each of the embodiments described above the foils support the whole of the weight of the vehicle and when the pig is travelling along the pipeline the foils are also subject to the reaction forces arising at the pipe wall owing to the movements of the vehicle in the pipeline.

In other embodiments (not shown) the foils may be required to support less than the entire weight of less than the full amount of such reactions from the wall, depending on the design of the vehicle.

However, in all embodiments the invention enables the available volumes to be efficiently used by the foils to transfer flux to and from the pipe wall. For the same suspension performance (i.e. support of some or all of the vehicle's weight and the wall reactions) relatively more metal to transfer flux can be accommodated in the available volume, so giving improved magnetic performance compared with steel bristles. Conversely, the vehicle has an improved bend passing performance (the vehicle being relatively short) with the same magnetic performance.

Design changes can be readily made. Foil replacement is simple and it is unnecessary to replace heavy plates such as form part of bristle brush assemblies. The force/deflection characteristics of the foils can be accurately predicted compared with bristles, for which empirical methods have to suffice.

Foils provide a path for flux from and to the magnet and can provide a suspension for the vehicle as well. Compared with bristles, they provide those features in less space for the same magnetic and suspension performance. This is important especially in vehicles for pipe inspection where high bend passing performance is a requirement. Compared with bristles, the foils behave in a more analytically predictable manner, because of foil independence. Foils are cheaper and more easily adjusted or tuned for a specific pipe bore range, and to suit a specific magnetic circuit, than are bristles.

The ratio of foil spacing to foil thickness controls the radial deflection (assuming the foils are mounted on a pipeline inspection vehicle) at which one foil comes into contact with its neighbour. This is a critical point beyond which all the foils "wedge up" giving an airgap to the pipe wall behind the leading foil. This effect is to be avoided during the normal inspection run of the vehicle. However, the effect is beneficial where the vehicle encounters a restricted pipe bore ("crash bore") because the magnetic drag is reduced by the air gap created. Within the normal bore range the suspension design must keep radial compressions of the foils well below this critical compression value.

By comparison, individual wire bristles within tufts of bristles tend to interfere with their neighbours right from zero radial deflection values, giving inherently poorer magnetic circuit completion. A ratio of foil spacing to foil thickness of 1:1 gives foil independency up to around 30% radial compression.

The extra drag caused by magnetic clamp forces at the foil tip cause a stiffening of the radial force/deflection characteristic. On "sweeps brush" inspection vehicles, this subtlety can be utilised to reduce overall vehicle drag by allowing the use of thinner foils. The magnetic drag helps to hold the vehicle up. Foils have the advantage of being viable in thinner sections, and this stiffening effect is more marked the greater the slenderness ratio. The designer hence has more scope with foils.

To avoid yielding over the relatively large deflections, a slenderness ratio of around 300 or more is necessary for ferritic materials.

Preinclined foils (optimally around 30 degrees), can further reduce base levels of drag without much change in stiffness (for the same initial radial reach). Where low drag is important this is worth doing. However, drag versus bore is not improved.

The invention is also applicable to inspection vehicles used for inspecting the condition of tank floors or bases. Where the tank floor is uneven the foils are required to yield or recover in a direction normal to the tank floor. This is what was referred to as radial compression or recovery in the case of a pipe inspection vehicle. Where the tank floor is made up of overlapping plates, the foils are required to yield and recover to accommodate such unevenness.

The invention is also applicable to magnetic inspection machines in which the magnet and foils assembly is moved over a plate which is to be inspected, or else the plate is moved past the magnet and foils assembly.

Figure 13:
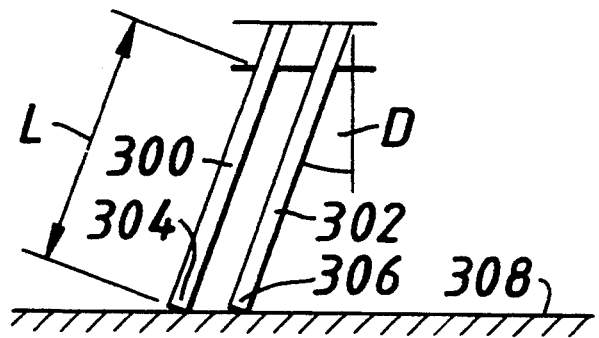
FIGS. 13 to 15 are scrap views of the foils and further illustrate the condition of the foils under increasing deflection.
Figure 14:
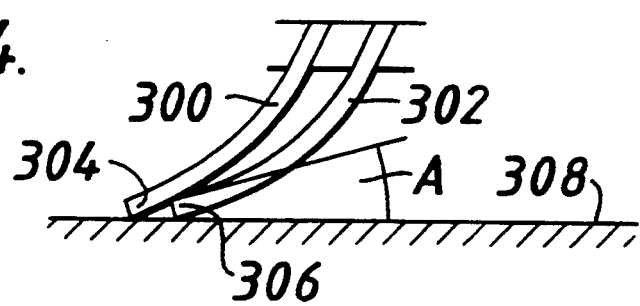
Figure 15:
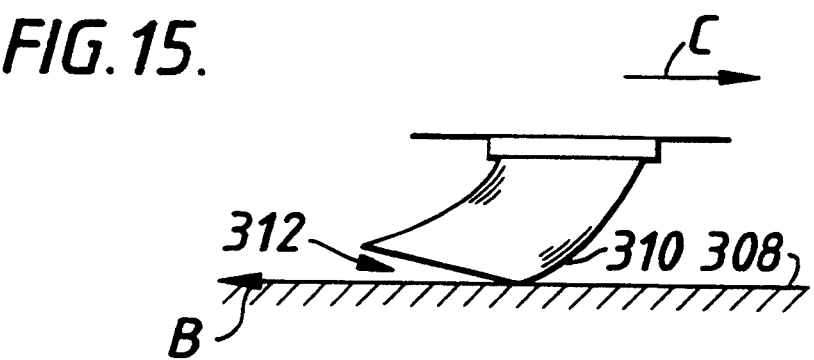

FIGS. 13 to 15 show foils of the swept back kind (see FIGS. 7-9 or FIGS. 10 to 12 for example). However, the following remarks would apply equally to foils which are planar in their undeflected state.

The figures show for illustration just two of the foils 300, 302 having tips 304, 306 which engage the workpiece 308, which may be the wall of a pipe or the base of a tank or a plate, depending on which machine is in use. The height of the foil in its undeflected state is "L". The thickness of the foil is "t" and the spacing between adjacent foils is "s".

FIG. 13 shows the foils in their undeflected state. FIG. 14 shows the foils when they have been deflected sufficiently for the tip 306 of one foil 302 to just engage the other foil 300. The angle "A" between the workpiece 308 and the tip 304 (which is the same for each foil) is then critical for the group of foils. Any further deflection leads to the position shown in FIG. 15.

In FIG. 15 all of the foils in a group have "wedged up" and the only foil which makes contact with the workpiece 308 is the leading foil, at 310. The remaining foils are lifted clear of the workpiece 308 and an airgap 312 is introduced into the magnetic circuit between the group of foils and the workpiece 308. The appearance of the airgap reduces the magnetic drag acting along the surface of the workpiece 308 in the direction of the arrow "B" in opposition to the direction "C" of travel of the vehicle.

The critical angle "A" is a function of the packing density s/t and, where the foils are swept back, of the sweepback angle "D". For realistic packing densities varying from 1 to 2, the limit varies between 30° to 20°. Up to that limit, no interference between neighbouring foils occurs (as would occur for tufts of wire bristles) and so the suspension characteristic of a whole assembly can be accurately calculated. Note also that up to this point there will be very little mechanical hysteresis. The compression (i.e. the radial stress, in the case of pipeline inspection) at which the limited angle is reached depends upon the deflection shape of the foil and this can be accurately calculated for any foil geometry and loading condition for all practical purposes it occurs in the region of 30% compression.

Yielding of the foil depends upon the slenderness ratio L/t of the foil. There is a minimum L/t ratio below which yielding will occur for a given material.

For a foil subjected to magnetic flux, it can be shown that for a saturated foil, the normalised magnetic clamp force varies as L/t, i.e. for the same L/t we get the same normalised characteristic. Hence, curves covering all foils can easily be produced. A normalised load is obtained by dividing the load value by the Euler buckling load for the foil. Then, for the case with no flux, and for a given coefficient of friction between the foil and the workpiece 308, and for a given sweepback "D", we always get the same normalised force/compression curve.

The characteristics of a suitable material for the foils are high yield stress, good magnetic properties (soft), availability in thin sections and preferably good rust resisting properties. Examples are EN 56A. (British Standard BS970 410S21); EN60 (BS 1449); EN57 (BS 1449, 2056, 1554); and EN43 (BS 1449).

We claim:

1. In a magnetic inspection machine constituting a first means and intended for progressively inspecting a workpiece constituting a second means during relative movement between said first and second means, a foil assembly for engaging the workpiece during said relative movement, said foil assembly comprising two groups of foils having tips which are intended to engage the workpiece and the groups being coupled magnetically at the ends of the foils remote from the tips to a source of magnetism, the foils being resiliently deflectable in a first direction transverse to the plane of the foil, each foil in each group being spaced from a neighbouring foil in said first direction by an intervening space and each foil in each group being separated from a neighbouring foil in a second direction transverse to said first direction by an intervening space allowing the foils to move closer to one another upon deflection of the foils caused by the distance between the first means and second means becoming less.

2. A machine according to claim 1 in which in each group there are a number of common foil members each of which is integral with several foils, the common foil members being spaced apart by intervening spacers so as to provide between neighbouring foils said intervening space.

3. A machine according to claim 1 the length of each foil being at least two hundred times its thickness and the quotient formed by dividing the separation between adjacent foils in each group by the foil thickness being in the range 1 to 2.

4. A machine according to claim 1 the foils being inclined so that even when undeflected their tips are positioned rearwardly with respect to their opposite inner ends in relation to the direction of working motion of the machine or rearwardly with respect to their opposite ends in relation to the direction of relative motion of the vehicle when the workpiece moves.

5. In a magnetic inspection machine constituting a first means and intended for progressively inspecting a workpiece constituting a second means during relative movement between said first and second means, a foil assembly for engaging the workpiece during said relative movement, said foil assembly comprising two groups of foils having tips which are intended to engage the workpiece and the groups being coupled magnetically at the ends of the foils remote from the tips to a source of magnetism, the foils being resiliently deflectable in a first direction transverse to the plane of the foil, each foil in each group being spaced from a neighbouring foil in said first direction by an intervening space and each foil in each group being separated from a neighbouring foil in a second direction transverse to said first direction by an intervening slot, said groups of foils each comprising a plurality of common foil members, said common foil members each being integral with a plurality of foils and being annular in shape, and said common foil members being spaced apart by intervening spacers so as to provide said intervening space between neighbouring foils.

6. In a magnetic inspection machine constituting a first means and intended for progressively inspecting a workpiece constituting a second means during relative movement between said first and second means, a foil assembly for engaging the workpiece during said relative movement, said foil assembly comprising two groups of foils having tips which are intended to engage the workpiece and the groups being coupled magnetically at the ends of the foils remote from the tips to a source of magnetism, the foils being resiliently deflectable in a first direction transverse to the plane of the foil, each foil in each group being spaced from a neighbouring foil in said first direction by an intervening space and each foil in each group being separated from a neighbouring foil in a second direction transverse to said first direction by an intervening slot, said groups of foils each comprising a plurality of common foil members, said common foil members each being integral with a plurality of foils and being sector-shaped, and said common foil members being spaced apart by intervening spacers so as to provide said intervening space between neighbouring foils.

7. In a magnetic inspection machine constituting a first means and intended for progressively inspecting a workpiece constituting a second means during relative movement between said first and second means, a foil assembly for engaging the workpiece during said relative movement, said foil assembly comprising two groups of foils having tips which are intended to engage the workpiece and the groups being coupled magnetically at the ends of the foils remote from the tips to a source of magnetism, the foils being resiliently deflectable in a first direction transverse to the plane of the foil, each foil in each group being spaced from a neighbouring foil in said first direction by an intervening space and each foil in each group being separated from a neighbouring foil in a second direction transverse to said first direction by an intervening slot, said groups of foils each comprising a plurality of common foil members, said common foil members each being integral with a plurality of foils and being annular in shape, and said common foil members being spaced apart by intervening spacers so as to provide said intervening space between neighbouring foils, each common foil member in each group being frusto-conical in shape.

8. In a magnetic inspection machine constituting a first means and intended for progressively inspecting a workpiece constituting a second means during relative movement between said first and second means, a foil assembly for engaging the workpiece during said relative movement, said foil assembly comprising two groups of foils having tips which are intended to engage the workpiece and the groups being coupled magnetically at the ends of the foils remote from the tips to a source of magnetism, the foils being resiliently deflectable in a first direction transverse to the plane of the foil, each foil in each group being spaced from a neighbouring foil in said first direction by an intervening space and each foil in each group being separated from a neighbouring foil in a second direction transverse to said first direction by an intervening slot, the widths of said intervening slots being such as to permit the foils of each group to come closer together in said second direction when said foils are deflected in said first direction.

* * * * *